(12) United States Patent
Fraschini (10) Patent No.: US 12,115,026 B2
(45) Date of Patent: Oct. 15, 2024

(54) METHOD AND SYSTEM FOR ESTIMATING AN ULTRASOUND ATTENUATION PARAMETER

(71) Applicant: SUPERSONIC IMAGINE, Aix-en-Provence (FR)

(72) Inventor: Christophe Fraschini, Aix-en-Provence (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 566 days.

(21) Appl. No.: 17/371,717

(22) Filed: Jul. 9, 2021

(65) Prior Publication Data

US 2022/0008044 A1 Jan. 13, 2022

(30) Foreign Application Priority Data

Jul. 10, 2020 (EP) .................................... 20315348

(51) Int. Cl.
*A61B 8/00* (2006.01)
*G06N 5/04* (2023.01)
*G06N 20/00* (2019.01)

(52) U.S. Cl.
CPC .............. *A61B 8/587* (2013.01); *G06N 5/04* (2013.01); *G06N 20/00* (2019.01)

(58) Field of Classification Search
CPC ........... A61B 8/587; G06N 20/00; G06N 5/04
See application file for complete search history.

(56) References Cited

U.S. PATENT DOCUMENTS

| 4,619,267 A | 10/1986 | Lannuzel et al. |
| 6,551,246 B1 | 4/2003 | Ustuner et al. |
| 11,607,197 B2 * | 3/2023 | Muller ............... A61B 5/02007 |
| 2008/0015439 A1 * | 1/2008 | Raju ..................... A61B 8/488 |
| | | 600/455 |

(Continued)

FOREIGN PATENT DOCUMENTS

| EP | 2 101 191 A2 | 9/2009 |
| JP | S60153849 A | 8/1985 |

(Continued)

OTHER PUBLICATIONS

Extended European Search Report for European Patent Application No. 20315348.1 mailed Dec. 11, 2020, 8 pages.

(Continued)

*Primary Examiner* — Dixomara Vargas
(74) *Attorney, Agent, or Firm* — Merchant & Gould, P.C.

(57) ABSTRACT

A method for estimating an ultrasonic attenuation parameter of a region in a medium includes a transmission step in which at least one pulse is transmitted in the medium by a transducer, and a reception step in which data is acquired by a transducer in response to the pulse. The method includes a processing step in which the data is processed by the processing unit for providing backscattered acquisition data of the region, and a function determination step in which an auto-correlation function of the backscattered acquisition data is determined which is a function of depth in the spatio-temporal domain, the autocorrelation function being determined at a lag of zero. The method includes an attenuation estimation step in which an ultrasonic attenuation parameter is estimated based on said auto-correlation function. The method is implemented by a processing unit associated to at least one ultrasound transducer.

19 Claims, 3 Drawing Sheets

(56) References Cited

U.S. PATENT DOCUMENTS

| | | | | |
|---|---|---|---|---|
| 2013/0144165 | A1* | 6/2013 | Ebbini | G01S 7/52046 |
| | | | | 600/439 |
| 2018/0263595 | A1* | 9/2018 | Goksel | A61B 8/085 |
| 2020/0129140 | A1* | 4/2020 | Raum | A61B 8/0875 |
| 2021/0321978 | A1* | 10/2021 | Nguyen | G06N 3/04 |
| 2021/0386404 | A1* | 12/2021 | Walker | A61B 8/5207 |
| 2023/0066217 | A1* | 3/2023 | Offerdahl | G01N 29/44 |
| 2023/0334911 | A1* | 10/2023 | Bhamidipati | G06T 7/50 |

FOREIGN PATENT DOCUMENTS

| | | |
|---|---|---|
| JP | S61-025536 A | 2/1986 |
| JP | 2020-39841 A | 3/2020 |
| KR | 10-2012-0071319 | 7/2012 |
| WO | 2017/093778 A1 | 6/2017 |
| WO | 2020/048875 A1 | 3/2020 |

OTHER PUBLICATIONS

Hyungsuk, K. et al., "Attenuation estimation using spectral cross-correlation", IEEE Transactions on Ultrasonics, Ferroelectrics and Frequency Control, 54(3): 510-519 (Mar. 2007).

Lymberis, A. et al., "Estimation of frequency-dependent attenuation based on parametric spectral analysis and correlation lags of the demodulated echo signal", Ultrasonic Imaging, 13(1): 1-26 (Jan. 1991).

* cited by examiner

METHOD AND SYSTEM FOR ESTIMATING AN ULTRASOUND ATTENUATION PARAMETER

This application claims benefit of European Patent Application Serial No. 20315348.1, filed 10 Jul. 2020 and which application is incorporated herein by reference. To the extent appropriate, a claim of priority is made to the above disclosed application.

BACKGROUND OF THE DISCLOSURE

Classical ultrasound imaging consists of an insonification of the medium with a cylindrical wave that focuses on a given point. Using the backscattered echoes of this single insonification, a complete line of the image is computed using a dynamic receive beamforming process. To build a complete image, this procedure is repeated by sending a set of focused waves that scan along a lateral line at given depth (named the focal plane). For each focused wave, a dynamic beamforming is performed, and the complete image is obtained, built line by line. The dynamic beamforming guarantees a uniform focusing in the receive mode, whereas, in the transmit mode the focus is fixed at a given depth. The final image is optimal in the focal plane and in a limited region of the medium corresponding to the focal axial length. However, outside this area, which is imposed by diffraction laws, the image quality is rapidly degraded at other depths (in the near and far fields of the focused beam).

SUMMARY OF THE DISCLOSURE

Currently, it remains desirable to overcome the aforementioned problems and in particular to provide a method and system for reliably estimating an ultrasonic attenuation parameter of a region in a medium, which advantageously may be faster, computationally less expensive and thus would require less processing power.

Therefore, according to the embodiments of the present disclosure, a method for estimating an ultrasonic attenuation parameter of a region in a medium is provided. Said method is implemented by a processing unit associated to at least one ultrasound transducer (which may be put in relation with said medium). The method comprises the following steps:
 (a) a transmission step in which at least one pulse is transmitted in the medium by a transducer,
 (b) a reception step in which data is acquired by a transducer in response to the pulse,
 (c) a processing step in which the data is processed by the processing unit for providing backscattered acquisition data of the region,
 (d) a function determination step in which an auto-correlation function of the backscattered acquisition data is determined which is a function of depth in the spatio-temporal domain, the autocorrelation function being determined at a lag of zero (0),
 (e) an attenuation estimation step in which an ultrasonic attenuation parameter is estimated based on said auto-correlation function.

Said method may also be referred to as a global attenuation estimation method, e.g. of one attenuation parameter for the examined complete region, e.g. for a complete ultrasound image.

By providing such a method, it becomes possible to estimate an ultrasound attenuation parameter by performing the analysis in the spatio-temporal domain instead of a frequency (or spectral) domain. Accordingly, the estimations are advantageously much more precise and imply less computational costs what improves e.g. a real time (or at least a quasi-real time) computation mode. Further, due to the increased preciseness a decreased variance and thus an increased reproducibility can be achieved.

The processing step (c) may comprise a beamforming step in which the data is processed by a beamforming process for providing beamformed acquisition data of the region. Said beamformed acquisition data or backscattered acquisition data may be presented in the form of e.g. pixels values, or voxels values.

Due to the beamforming process it becomes possible to reduce the diffraction pattern in the acquired data.

The beamforming process may be for example a synthetic beamforming process. This allows to further reduce the diffraction pattern.

Moreover, it is possible to configure the beamforming process of step of c) to further reduce speckle noise. For example, step (c) may comprise:
 (c1) a beamforming step in which the data is processed by a plurality of beamforming processes for providing beamformed acquisition data of at least the region, each beamforming process either using a data corresponding to a pulse generated with a transmit weighting vector, or using a transmit weighting vector in the calculus of the beamformed acquisition data, and
 (c2) a combining step in which the beamformed acquisition data of said plurality are combined to provide a pixel value of a pixel inside a generated ultrasound image, and wherein the transmit weighting vectors are different and orthogonal one to another one.

However, an alternative process to the beamforming process described above may be used, to provide backscattered acquisition data. For example, acoustic beam shaping of the transmitted pulse (and optionally the received signal) via acoustic lens or mechanical sweeping/scanning might be employed. In such a case, a beamforming process may be omitted in the processing step (c).

In the attenuation estimation step (e), an ultrasonic attenuation parameter may be estimated over an interval $\Delta z$ in the depth direction. For example, said interval $\Delta z$ may be predefined between a first and a second specified depth in the medium. It has to be noted that depth in the medium may be defined as the distance between the surface of the probe and the point (spatial location) of interest.

In the attenuation determination step, the ultrasonic attenuation parameter may be determined by solving the auto-correlation function, e.g. for the interval $\Delta z$.

The auto-correlation function of the backscattered acquisition data may be a function of depth and of time.

In the function determination step (d) a residual diffraction pattern in the backscattered acquisition data may be compensated based on predetermined diffraction reference data.

A residual diffraction pattern in the backscattered acquisition data is compensated by applying a method comprising steps (a') to (e') on a reference medium having a predetermined reference ultrasonic attenuation parameter and comparing the auto-correlation functions.

In other words, the estimation method may be applied on such a reference medium, e.g. a phantom, with a predetermined, i.e. known ultrasonic attenuation parameter. Accordingly, the determined auto-correlation function which may be referred to as a reference auto-correlation function, may be solved to determine the residual diffraction pattern in the backscattered acquisition data and/or compensate it in the auto-correlation function of the medium including the region of interest to be examined.

Comparing the auto-correlation functions may comprise calculating a delta function between both functions and solving the delta function to determine the ultrasonic attenuation parameter of the medium.

For example, the reference ultrasonic attenuation parameter may be a parameter for an interval $\Delta z'$ in the reference medium similar to the interval $\Delta z$ in the medium to be examined.

The predetermined diffraction reference data may comprise predetermined parameters for different depths in the reference medium.

The pulse may be a wide band pulse and/or a plurality of pulses. For example, the use of a wide band pulse (or wide band pulses) may increase the estimation preciseness as it allows a spatial limitation, i.e. a more precise interval determination.

The present disclosure further relates to a method for estimating local ultrasonic attenuation parameters of a region in a medium. Said method may comprise the global attenuation estimation method described above (i.e. the steps (a) to (e)). For each of a plurality of axial lines (e.g. lines scanned in steps (a) to (c)) in the depth direction z within the medium, a local ultrasonic attenuation B is estimated in an equation $F(Ey(z),B)=0$, Ey being the auto-correlation function, z the depth, by at least one of the following methods:
  modelling the auto-correlation function as a noisy state space model with a driving input,
  regularizing the auto-correlation function by a regularization method comprising: a Tikhonov regularization method, a ridge regression method, and/or Bayesian regression method,
  filtering the auto-correlation function with a Savitzky-Golay filter, a Monte Carlo method,
  a Singular Spectrum analysis, and
  a compressed sensing and/or sparse sampling method.

Said method may also be referred to as a local attenuation estimation method, e.g. of a plurality of attenuation parameters for the complete examined region, e.g. for one ultrasound image. Said parameters may be assigned to pixels or voxels in an ultrasound image. They may also form segments or super-pixels or clusters in an ultrasound image of an additionally attenuation map of the examined region.

Thanks to this method, it becomes possible to estimate local ultrasonic attenuation parameters for the region of interest, allowing creating a map and/or image(s) of the attenuation characteristics across the region.

In comparison to a conventional inversion method which might be used for solving equation $F(Ey(z), B)$, the proposed methods imply less calculation effort, as they converge faster. At the same time, they lead to more precise results, e.g. to a higher spatial resolution of obtained local estimations.

The auto-correlation function may be discretized in depth direction (z) for obtaining the local attenuation function.

The driving input may comprise the predetermined attenuation parameter of the reference medium.

The modelized state space model may use a Kalman filter or a predefined Bayesian method to determine the local ultrasonic attenuation parameters.

The use of a Kalman filter may have the advantage to optimize the minimum mean square error criteria.

A reflectivity pattern of the medium may be compensated by iterating an EM algorithm on the modelized state space model until a predefined converging threshold is obtained.

For example, the EM algorithm may use a first Kalman filter which outputs a reflectivity parameter and may use an ultrasound attenuation parameter as a driving input. A second Kalman filter may output an ultrasound attenuation parameter and may use a reflectivity parameter as a driving input. Both filters may be connected to respectively use the output of the other one as a driving input, e.g. until the predefined converging threshold is obtained.

The present disclosure further relates to a method for imaging a local ultrasonic attenuation within a region of a medium. The method may comprise the local attenuation estimation method as described above. An attenuation image may be built based on the local attenuation parameters, e.g. for each axial line.

The method for imaging a local ultrasonic attenuation within a region of a medium may further comprise the steps of feeding the attenuation image into a machine learning model which is trained to segment the image into one or several regions of interest which are respectively associated with at least one predefined category.

Said machine learning model may comprise e.g. an artificial neural network e.g. a Convolutional neural network (the model may be e.g. computer implemented). The model may be trained by a supervised training method using e.g. respectively annotated images as training data, or by an unsupervised training method.

Finally, the present disclosure relates to a system for estimating an ultrasonic attenuation parameter of a region in a medium, comprising a processing unit associated or connected to at least one ultrasound transducer (2) (e.g. in relation with said medium). The system or the processing unit is configured to:
  (a) transmit at least one pulse in the medium by a transducer,
  (b) acquire data by a transducer in response to the pulse,
  (c) process data by the processing unit for providing backscattered acquisition data of the region,
  (d) determine an auto-correlation function of the backscattered acquisition data which is a function of depth in the spatio-temporal domain, the autocorrelation function being determined at a lag of zero (0),
  (e) estimate an ultrasonic attenuation parameter based on said auto-correlation function.

The system may optionally also comprise the at least one transducer.

The at least one transducer may be a single transducer configured to transmit a pulse and receive the tissue response. For example, a focalized transducer, having e.g. a concave form or a respective lens. It is additionally possible to sweep the single transducer.

It is also possible to use a plurality of transducers and/or a transducer array 2. For example, a linear array may be provided typically including a few tens of transducers (for instance 100 to 300) juxtaposed along an axis X (horizontal or array direction X). 3D probes may also be used for implementation of the present disclosure.

The same transducer(s) may be used to transmit a pulse and receive the response, or different transducers are used for transmission and reception.

The present disclosure may further relate to a computer program including instructions for executing the steps of at least one of the methods described above, when said program is executed by a computer.

Finally, the present disclosure may also relate to a recording medium readable by a computer and having recorded thereon a computer program including instructions for executing the steps of at least one of the methods described above, when said program is executed by a computer.

It is intended that combinations of the above-described elements and those within the specification may be made, except where otherwise contradictory.

It is to be understood that both the foregoing general description and the following detailed description are exemplary and explanatory only, are provided for illustration purposes and are not restrictive of the disclosure, as claimed.

The accompanying drawings, which are incorporated in and constitute a part of this specification, illustrate embodiments of the disclosure and together with the description, and serve to support and illustrate the principles thereof.

DESCRIPTION OF THE EMBODIMENTS

To overcome limitations identified in the Background, a classical solution is to perform multi-focus imaging: different transmit focal depths are used to obtain a homogeneous quality all over the image. Each transmission at a given focal depth enables performing a partial image in the region delimited by the axial focal length. The final image is obtained using a recombination of these partial images corresponding to various depths. An optimal multi-focus image requires typically tens of focal planes. This leads to frame rate limitations, typically <10 frames/second, that are not acceptable for ultrasound imaging. A good compromise between image quality and frame rate is around 4 focal depths images.

Improvement in image quality can be envisioned by performing synthetic dynamic transmit focalization. Such approach consists in re-synthesizing a dynamic transmit focusing (i.e. as many focal depths as pixel in the image) by beamforming and then combining a set of different insonifications.

Moreover, an improved synthetic ultrasound imaging method is known from EP2101191 (A2) filed by the applicant, which enables to improve conventional plane wave synthetic ultrasound imaging methods as disclosed for example by U.S. Pat. No. 6,551,246.

European patent application EP2101191 (A2) proposes a method for ultrasound imaging which comprises at least the following steps:
 a) a transmission step in which a plurality of ultrasonic waves are transmitted into an imaged region and a respective set of raw data is acquired by an array of transducers in response to each ultrasonic wave, said ultrasonic waves having different spatial frequency content, for each of a plurality of imaged locations in the region, each set of raw data representing the time signals received by the transducers in response to the corresponding ultrasonic wave;
 b) a coherence enhancing step in which, for each of a plurality of virtual transmit focal zones in the imaged region, at least one set of coherent data is synthesized from the sets of raw data;
 c) a beamforming step in which, for each of a plurality of locations included in each of the virtual transmit focal zones, an image pixel is computed by beamforming, using the set of coherent data.

Thanks to these dispositions, the spatial coherence of the raw data is recovered at step b) prior to beamforming, thus enabling to accurately combine the data received from the transmission of the various ultrasonic waves. The need to recover spatial coherence is due to the fact that, when illuminating the imaged region with spatially widely spread wavefield, the echoes coming back from the medium can be seen as a wavefield originating from incoherent sources (the scatterers), randomly distributed in the imaged region: thus, the spatial coherence of the wavefield is lost (or very poor) in the raw data. The beamforming may then be performed on the coherent data resulting from the coherence recovery step, resulting in a more accurate image.

Based on this technique, which may be referred to as synthetic beamforming, WO2017093778 (A1) discloses another imaging method for producing an image of a region inside a medium, having a reduced speckle noise. To this effect, the method comprises the following steps:
 (a) a transmission step in which a first plurality of waves is transmitted inside the medium by the transducers,
 (b) a reception step in which a set of data is acquired by said transducers in response to the waves,
 (c) a beamforming step in which the set of data is processed by a second plurality of beamforming processes for providing beamformed pixel values of at least a portion of the image, each beamforming process either using a set of data corresponding to waves generated with a transmit weighting vector, or using a transmit weighting vector in the calculus of the beamformed pixel value, and
 (d) a combining step in which the beamformed pixel values of said second plurality are combined to provide a pixel value of a pixel inside the image, and wherein the transmit weighting vectors are different and orthogonal one to another one.

Thanks to these features, each transmit weighting vector generates an uncorrelated speckle noise, and the combination of the weighted data allow to compute an image of the region having a reduced speckle noise.

However, a further phenomenon in ultrasound imaging, which desirably has to be considered, is ultrasound attenuation within an examined medium. Ultrasound attenuation directly affects the response to transmitted ultrasound waves. Attenuation thereby constitutes a subtle frequency and depth dependent phenomenon. It is thus desirable to compensate any effects of attenuation on the resulting computed image, as it is conventionally done by e.g. time-gain compensation to account for tissue attenuation.

On the other hand, a reliable estimation of ultrasound attenuation may be used for other ultrasound diagnosis purposes. For example, a global attenuation parameter estimated for the examined medium, e.g. a human liver or muscle, may serve for determining its fat content. Moreover, a local attenuation distribution, e.g. processed to compute an image, may serve for detecting cancers, e.g. in a human breast.

However, conventional methods for estimating ultrasound attenuation usually employ frequency (or spectral) analysis. Such analysis though implies several disadvantages.

Since attenuation is a subtle frequency and depth dependent phenomenon, accurate assessment needs sufficiently large spatial and frequency observation range. This means that one would like to use large frequency and spatial range. However, because of the attenuation, the larger the spatial range the larger frequency content variation, and the larger the bias. On the other hand, the smaller the spatial range, the poorer the spectral analysis. Furthermore, the larger the spatial range, the larger the impact of the diffraction. Moreover, speckle noise increases attenuation estimate variance.

Accordingly, in view of this necessary trade-off, estimating ultrasound attenuation by frequency (or spectral) analysis leads to unprecise results and at the same time requires significant computational costs, in particular due to required Fourier transformations. As a consequence, there are the problems of an increased variance of possible results and hence a decreased reliability of the estimations, i.e. a decreased reproducibility. Therefore, a trade-off between acquisition time and level of precision must be made.

A. Lymberis et. al. proposes a method for estimating frequency-dependent attenuation. In particular in proposed method 2 a mean frequency estimator derived from all the available autocorrelation lags (ACn) of the demodulated signal, cf. LYMBERIS ET AL: "Estimation of frequency-dependent attenuation based on parametric spectral analysis and correlation lags of the demodulated echo signal", ULTRASONIC IMAGING, DYNAMEDIA INC., SILVER SPRING, MD, US, vol. 13, no. 1, 1 Jan. 1991 (Jan. 1, 1991), pages 1-26, XP026409816, ISSN: 0161-7346.

Moreover, Hyungsuk et. al discloses an attenuation estimation method using spectral cross-correlation, cf. HYUNGSUK KIM ET AL: "Attenuation estimation using spectral cross-correlation", IEEE TRANSACTIONS ON ULTRASONICS, FERROELECTRICS AND FREQUENCY CONTROL, IEEE, US, vol. 54, no. 3, 1 Mar. 2007 (Mar. 1, 2007), pages 510-519, XP011175817, ISSN: 0885-3010, DOI: 10.1109/TUFFC.2007.274.

The technologies described herein relate to imaging methods and apparatus implementing said methods, in particular for medical imaging. In an example, a method is described for estimating ultrasound attenuation parameter of a region in a medium.

In another example, a method is described for estimating and imaging local ultrasonic attenuation parameters of a region inside a medium. The methods may be implemented by a processing unit associated to a plurality (e.g. a line or an array) of transducers in relation with said medium.

Reference will now be made in detail to exemplary embodiments of the disclosure, examples of which are illustrated in the accompanying drawings. Wherever possible, the same reference numbers will be used throughout the drawings to refer to the same or like parts.

Figure 1:
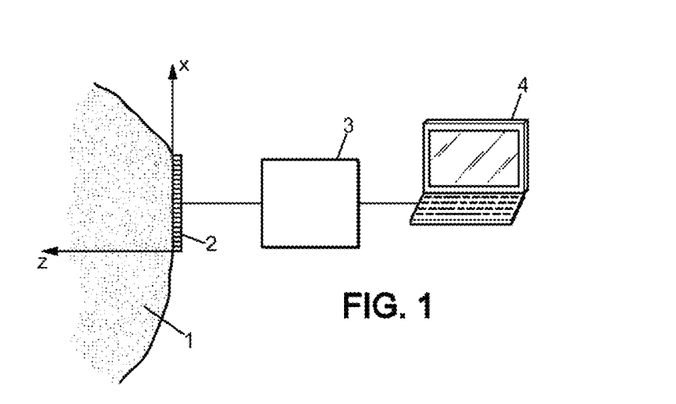
FIG. 1 shows a schematic drawing showing an ultrasound apparatus according to embodiments of the present disclosure.

The apparatus shown on FIG. 1 is adapted for imaging of a region 1 of a medium, for instance living tissues and in particular human tissues of a patient.

The apparatus may include for instance:

at least one transducer, e.g. a single transducer configured to transmit a pulse and receive the tissue response. Also, it is possible to use a plurality of transducers and/or a transducer array 2. For example, a linear array may be provided typically including a few tens of transducers (for instance 100 to 300) juxtaposed along an axis X (horizontal or array direction X) as already known in usual probes. In this case the array 2 is adapted to perform a bidimensional (2D) imaging of the region 1, but the array 2 could also be a bidimensional array adapted to perform a 3D imaging of the region 1. The transducer array 2 may also be a convex array including a plurality of transducers aligned along a curved line. The same transducer(s) may be used to transmit a pulse and receive the response, or different transducers are used for transmission and reception;

an electronic bay 3 controlling the transducer array and acquiring signals therefrom;

a microcomputer 4 for controlling the electronic bay 3 and e.g. viewing images obtained from the electronic bay (in a variant, a single electronic device could fulfil all the functionalities of the electronic bay 3 and of the microcomputer 4).

The axis Z on FIG. 1 is an axis perpendicular to the axis X, and it is usually the direction of ultrasound beams generated by the transducers of the array, e.g. in the depth direction of the examined medium. This direction is designated in present document as a vertical or axial direction.

Figure 2:
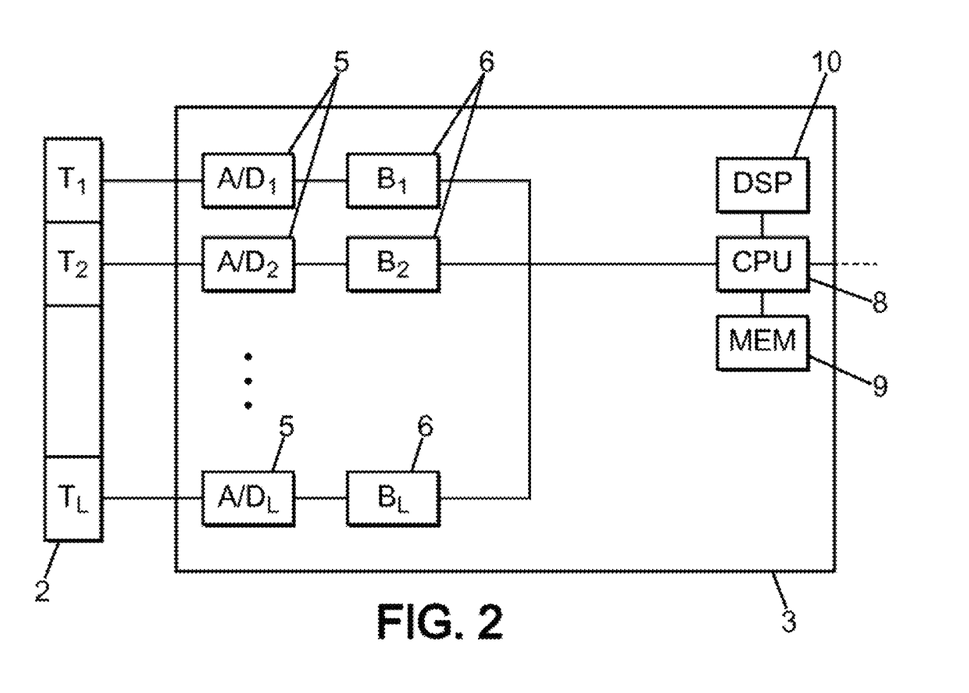
FIG. 2 shows a block diagram showing part of the apparatus of FIG. 1.

As shown on FIG. 2, the electronic bay 3 may include for instance:

L analog/digital converters 5 (A/Di-A/DL) individually connected to the L transducers (Tl-TL) of the transducer array 2;

L buffer memories 6 (Bi-Bn) respectively connected to the n analog/digital converters 5, a central processing unit 8 (CPU) communicating with the buffer memories 6 and the microcomputer 4, a memory 9 (MEM) connected to the central processing unit 8;

a digital signal processor 10 (DSP) connected to the central processing unit 8.

The apparatus herein disclosed is a device for ultrasound imaging, the transducers are ultrasound transducers, and the implemented method estimates an ultrasonic attenuation parameter for region 1 and optionally may produce ultrasound images of region 1.

However, the apparatus may be any imaging device using other waves than ultrasound waves (waves having a wavelength different than an ultrasound wavelength), the transducers and the electronic bay components being then adapted to said waves.

Figure 3:
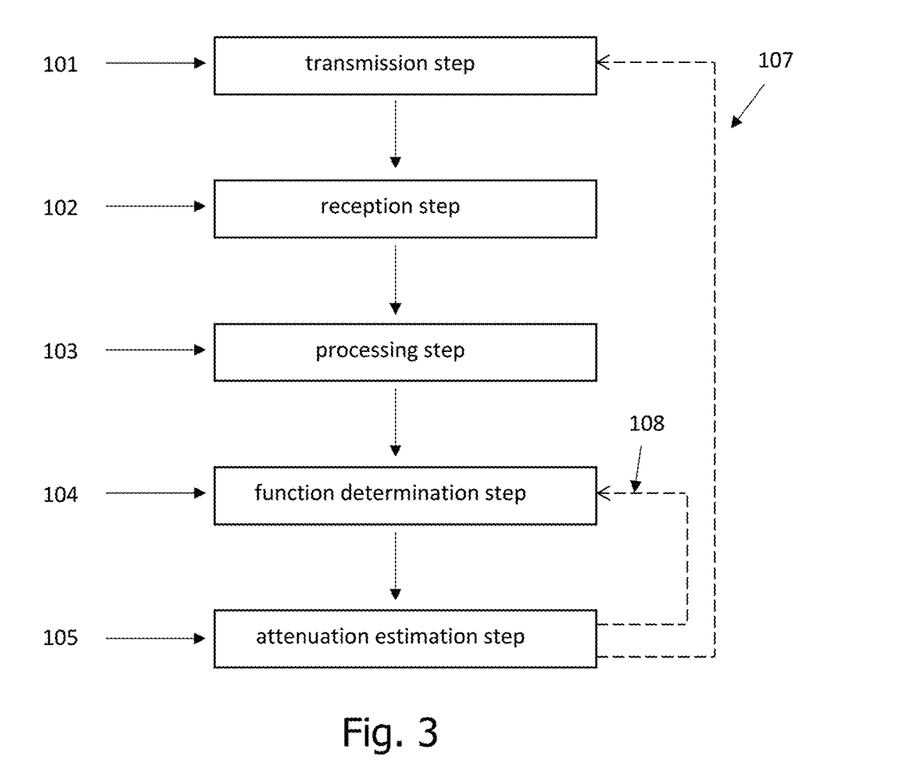
FIG. 3 shows a diagram of method for estimating an ultrasound attenuation parameter according to the present disclosure and implemented in the apparatus of FIG. 1.

FIG. 3 shows a diagram of a method for estimating an ultrasound attenuation parameter according to the present disclosure and implemented in the apparatus of FIG. 1.

The method steps are controlled mainly by the central processing unit 8 eventually with the help of the digital signal processor 10, or any other means. The method includes the following main steps:

(a) a transmission step (101) in which at least one pulse is transmitted in the medium by a transducer, (b) a reception step (102) in which data is acquired by a transducer in response to the pulse, (c) a processing step (103) in which the data is processed by the processing unit for providing backscattered acquisition data of the region, (d) a function determination step (104) in which an auto-correlation function of the backscattered acquisition data is determined which is a function of depth in the spatio-temporal domain, (e) an attenuation estimation step (105) in which an ultrasonic attenuation parameter is estimated based on said auto-correlation function.

Optionally also an ultrasound image may be produced based on the backscattered acquisition data of step 103.

For example, the estimated ultrasound attenuation parameter may be used to:

Evaluate liver steatosis when it provides a global estimator,

Detect Duchenne Muscular Dystrophy carriers when it provides a global estimator, and/or characterize breast masse(s) when it provides a map of attenuation.

Those examples are provided as illustration applications of the method described in this disclosure, but other applications e.g. related to an animal's body, and/or material analysis may be of interest as well.

Steps 101 to 105 may optionally form a loop, e.g. a loop 107 by returning back from step 105 to 101. This may allow the estimation of a plurality of attenuation parameters, wherein as an option in step 103 in each cycle additionally an ultrasound image may be produced. It is additionally or alternatively possible to add a loop 108 to loop steps 104 and 105 by returning from step 105 to 104. This may allow to estimate a plurality of local estimations (optionally at different areas of the region of interest), as described in more detail in context of FIG. 6.

Figure 4:
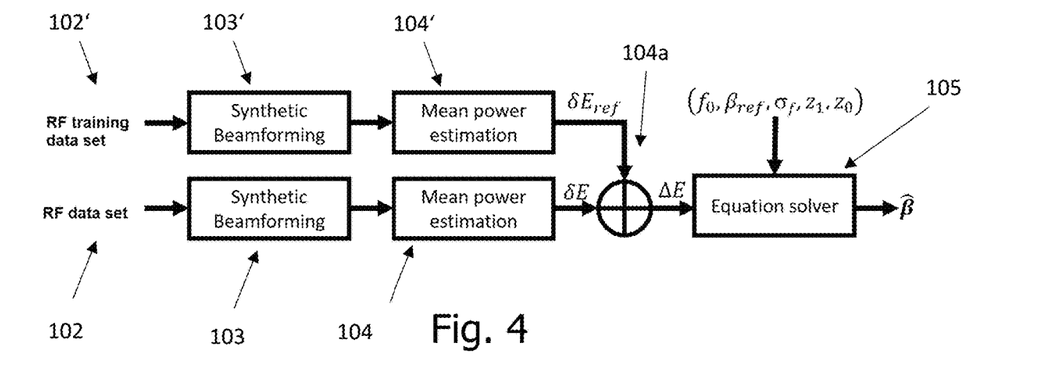
FIG. 4 shows a diagram of a first exemplary embodiment (global attenuation estimation) of the method according to the present disclosure.
Figure 5:
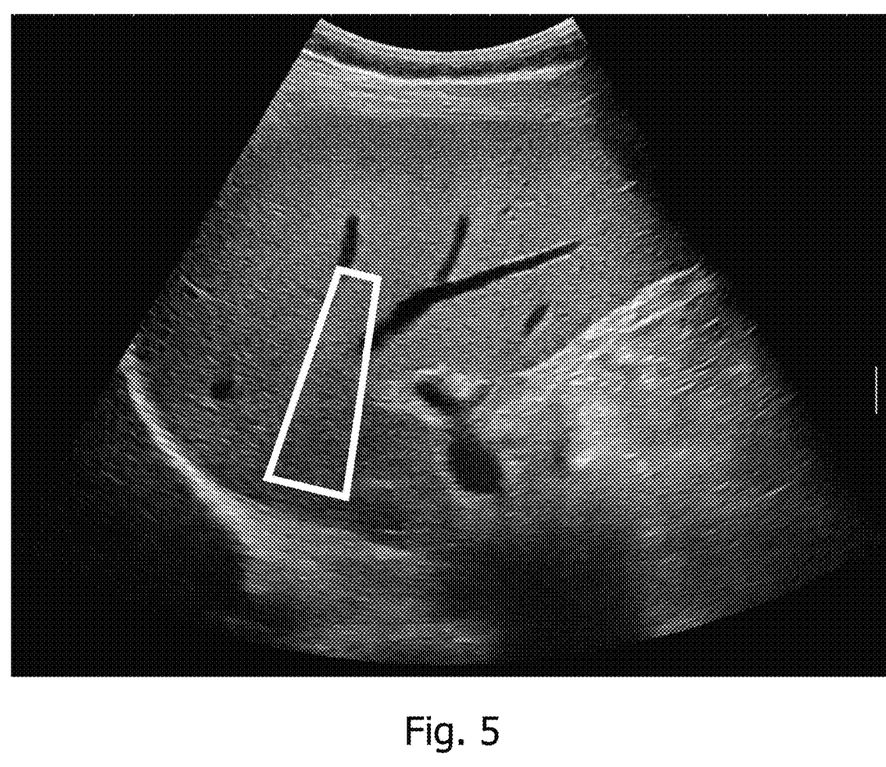
FIG. 5 shows an example of an ultrasound image obtained by the method of FIG. 3 or 4.
Figure 6:
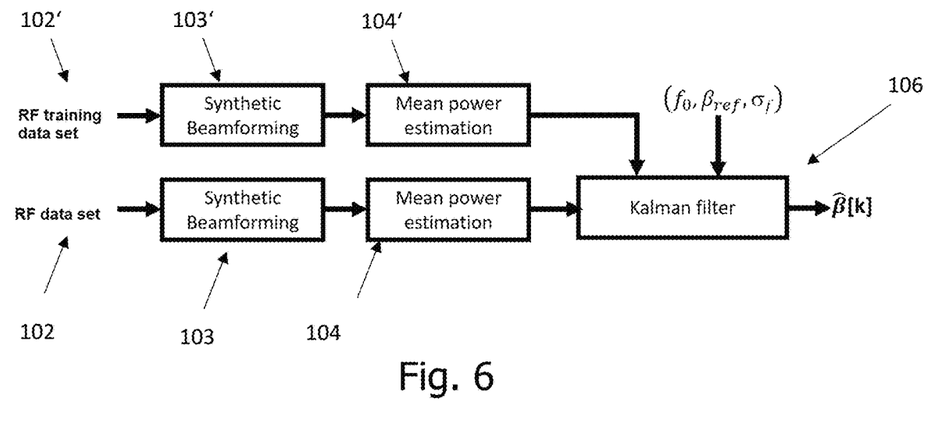
FIG. 6 shows a diagram of a second exemplary embodiment (local attenuation estimation) of the method according to the present disclosure.

In some embodiments, said method may serve for estimating a global ultrasound attenuation parameter, as described on more detail in context of FIGS. 4 and 5 or a local ultrasound attenuation parameter, as described in context of FIG. 6. However, before describing the detailed embodiments of the present disclosure in detail, some basics are provided in the following.

The following description uses the glossary below:

ACF: Auto Correlation Function
$\beta$: ultrasound attenuation (dB/cm/MHz or Np/cm/MHz)
C: speed of sound in the medium
$f_0$: center frequency of the pulse
$\lambda$: wavelength of the pulse ($\lambda = c/f_0$)
MMSE: Minimum Mean Square Error
PSD: Power Spectral Density
ROI: Region Of Interest
RF data: two-dimensional array (transducers versus time) storing the digitalized signals acquired on the probe
$\sigma_f$: Standard deviation of the gaussian shaped spectrum It is assumed in the following that the medium is homogeneous and contain weak scatterers. The analytic signal of the transmitted pulse is supposed to have a gaussian envelope and center frequency $f_0$:

$$x(t) = e^{\frac{t^2}{2\sigma_s^2}} e^{-2i\pi f_0 t} \tag{1}$$

In the following, the general signal modelling which may be used in the present disclosure is described. The signal modelling is thereby progressively enhanced by progressively adding to the model: ultrasound echoes (i.e. PSD), ultrasound attenuation, diffraction, reflectivity.

First, it is described how Power Signal Density (PSD) measured on pixels may be modelled. In this description section, the ultrasound attenuation is not taken into consideration for simplicity reasons. For focused aperture, the signal backscattered by the isochronous volume at time t can be modelled as:

$$s(t) = s_0 n(t) * \left[ e^{\frac{t^2}{2\sigma_s^2}} e^{-2i\pi f_0 t} \right] \tag{2}$$

where n(t) is a zero-mean gaussian stochastic process with microscopic autocorrelation function, i.e.:

$$E\{n(t)n^*(t+\tau)\} = \gamma\delta(\tau) \tag{3}$$

Accordingly, the expression of the autocorrelation function of the backscattered signal may be formulated as follows:

$$E\{s(t)s^*(t+\tau)\} = s_0^2 E\left\{ n(t) * \left[ e^{\frac{t^2}{2\sigma_s^2}} e^{-2i\pi f_0 t} \right] s^*(t+\tau) \right\} \tag{4}$$

$$E\{s(t)s^*(t+\tau)\} = s_0^2 E\{n(t)s^*(t+\tau)\} * \left[ e^{\frac{t^2}{2\sigma_s^2}} e^{-2i\pi f_0 t} \right]$$

$$E\{s(t)s^*(t+\tau)\} =$$

$$s_0^2 E\left\{ n(\tau)n^*(t+\tau) * \left[ e^{\frac{(t+\tau)^2}{2\sigma_s^2}} e^{2i\pi f_0(t+\tau)} \right] \right\} * \left[ e^{\frac{t^2}{2\sigma_s^2}} e^{-2i\pi f_0 t} \right]$$

$$E\{s(t)s^*(t+\tau)\} = s_0^2 \gamma \delta(\tau) * \left[ e^{\frac{t^2}{2\sigma_s^2}} e^{-2i\pi f_0 t} \right] * \left[ e^{\frac{(t+\tau)^2}{2\sigma_s^2}} e^{2i\pi f_0(t+\tau)} \right]$$

$$E\{s(t)s^*(t+\tau)\} = s_0^2 \gamma \sqrt{\frac{2}{\pi}} \sigma_s e^{\frac{t^2}{4\sigma_s^2}} e^{-2i\pi f_0 \tau}$$

Using Wiener-Kintchine theorem, the PSD S(f) of the backscattered signals can be expressed as:

$$S(f) = TF[E\{s(t)s^*(t+\tau)\}] \tag{5}$$

$$S(f) = 2\sqrt{2}\,\sigma_s^2 s_0^2 \gamma e^{-4\pi^2 \sigma_s^2 (f-f_0)^2}$$

$$S(f) = \frac{s_0^2 \gamma}{4\pi\sqrt{2}\,\sigma_f^2} e^{-\frac{(f-f_0)^2}{2\sigma_f^2}}$$

The beamforming process consists in accumulating signals acquired on transducers at delays that correspond to the propagation time from the pixel of interest to the transducers. Hence, the PSD measured on a pixel is given by equation (5).

Next it is described, how ultrasound attenuation may be modelled. In particular, ultrasound attenuation may be modelled as a filter with the following transfer function.

$$|H(f,z)| = e^{-2\beta f z} \tag{6}$$

Coefficient 2 stands for the round-trip propagation. Assuming axial transmit and receive beams, the combination of (5) and (6) leads to the expression of the PSD of a beamformed pixel at depth z:

$$S(f,z) = \frac{s_0^2 \gamma}{\sqrt{2\pi}\,\sigma_f} e^{-\frac{(f-f_0)^2 + 4\beta f z \cdot 2\sigma_f^2}{2\sigma_f^2}} \tag{7}$$

$$S(f,z) = \frac{s_0^2 \gamma}{4\pi\sqrt{2}\,\sigma_f^2} e^{-\frac{(f-f_r)^2}{2\sigma_f^2}} e^{-\frac{f_r^2 - f_0^2}{2\sigma_f^2}}$$

Where $f_r = f_0 - 4\beta\sigma_f^2 z$

Invoking Wiener-Kintchine theorem from spectral to spatio-temporal domain on the PSD given by equation (7) leads to $$R(\tau, z) = E\{s(t, z)s^*(t+\tau, z)\} = TF^{-1}\{S(f, z)\} \quad (8)$$

$$R(\tau, z) = \frac{1}{4\sqrt{\pi}\sigma_f} \int_{-\infty}^{+\infty} e^{-2i\pi f\tau} \frac{s_0^2 \gamma}{\sqrt{2\pi}\sigma_f} e^{-\frac{(f-f_r)^2}{2\sigma_f^2}} e^{-\frac{f_r^2 - f_0^2}{2\sigma_f^2}} df$$

$$R(\tau, z) = \frac{1}{4\sqrt{\pi}\sigma_f} e^{-\frac{f_r^2 - f_0^2}{2\sigma_f^2}} \int_{-\infty}^{+\infty} e^{-2i\pi f\tau} \frac{s_0^2 \gamma}{\sqrt{2\pi}\sigma_f} e^{-\frac{(f-f_r)^2}{2\sigma_f^2}} df$$

The ACF taken at lag $\tau=0$ gives the mean power of the pixel value. Using equation (8) yields:

$$E(z) = R(0, z) \quad (9)$$

$$E(z) = \frac{1}{4\sqrt{\pi}\sigma_f} s_0^2 \gamma e^{\frac{f_r^2 - f_0^2}{2\sigma_f^2}} \int_{-\infty}^{+\infty} \frac{1}{\sqrt{2\pi}\sigma_f} e^{-\frac{(f-f_r)^2}{2\sigma_f^2}} df$$

$$E(z) = \frac{1}{4\sqrt{\pi}\sigma_f} s_0^2 \gamma e^{\frac{f_r^2 - f_0^2}{2\sigma_f^2}} \quad (10)$$

Passing from (9) to (10) is justified by the fact that the right-hand side of (9) is the integral of a Gaussian function from $-\infty$ to $+\infty$, and hence, it integrates to 1.

Next it is described, how a complete pixel signal may be modelled. Taking into consideration the transducers sensitivity, beamforming antenna gain, diffraction, and combining with equation (10) leads to the following expression:

$$\ln[E(z)] = \frac{f_r^2 - f_0^2}{2\sigma_f^2} + \text{constant}(z)$$

$$\boxed{\ln[E(z)] = -4\beta f_0 z + 8\beta^2 \sigma_f^2 z^2 + \text{constant}(z)} \quad (11)$$

Equations (11) represents the core of the method described in that document. In that framework, constant(z) is estimated.

It has been found by the inventor of this disclosure that an ultrasound attenuation estimation method based on equation (11) present the following advantages:
Less sensitive to diffraction effects because
  It operates on synthetic beamformed data; hence both transmit and receive focus are ensured at any spatial location
  It operates in the spatiotemporal domain and diffraction effects are averaged over the frequency range of the pulse
  The transmitted pulse is wide band
It does not need a time (or spatial) frequency compromise like frequency-based methods do.
Local energy estimation on beamformed data is easy and robust, as a result attenuation estimator is more robust.

With reference to FIG. 4, a method for estimating a global ultrasound attenuation parameter is described. Accordingly, FIG. 4 shows a diagram of a first exemplary embodiment (global attenuation estimation) of the method according to the present disclosure. In particular, the method of FIG. 4 may be a specific embodiment of the method of FIG. 3.

The method of FIG. 4 starts with the reception step b, here reference numerals 102 and 102', in which data is acquired by a transducer in response to the pulse. This data is referred to here as "RF data set" for the examined medium, and "RF training data set" for the reference medium, e.g. a phantom. Steps 102-104 refer to the processing of data of the examined medium, meanwhile similar steps 102'-104' refer to the processing of data of the reference medium.

The next steps 103, and 103' "Synthetic Beamforming" respectively corresponds to step (c) of the present disclosure and FIG. 3, i.e. a processing step in which the data is processed by the processing unit for providing backscattered acquisition data of the region.

The next steps 104, 104' "Mean power estimation" respectively corresponds to step (d) of the present disclosure and FIG. 3, i.e. a function determination step in which an auto-correlation function of the backscattered acquisition data (in particular the beamformed acquisition data of step 103) is determined which is a function of depth in the spatio-temporal domain.

In a next step 104a, the two auto-correlation functions are compared with each other to compensate a diffraction pattern in the backscattered acquisition data and/or an unknown transducer sensitivity. In particular, a delta function may be determined between both functions. An exemplary embodiment of said comparison step is described below.

In step 105 an ultrasonic attenuation parameter is estimated by solving the comparison of the two auto-correlation functions, i.e. in particular their delta function. In more details:
In the following description, basic assumptions are made:
The attenuation in the medium is constant and
constant(z) in equation (11) does not depend on z, i.e. it is constant over the region of interest ROI.

The goal of the methods of FIGS. 3 and 4 is to estimate $\beta$ in a specific ROI. The ROI could be a homogeneous portion of a liver as depicted on FIG. 5.

Let $z_0$ and $z_1$ (respectively) denote the depth of the top and the bottom (respectively) of the ROI. Depth means distance between the surface of the probe and the point (spatial location) of interest.

Evaluating the difference of the logarithm of the mean powers at depth z0 and z1 yields $$\delta E(z_0, z_1) = -4\beta f_0(z_1 - z_0) + 8\beta^2 \sigma_f^2(z_1^2 - z_0^2) + \text{constant}(z_1, z_0) \quad (12)$$

Equation (12) (which may be understood as the result of step 104) includes 2 unknowns: constant($z_1$, $z_0$) and $\beta$.

To estimate $\beta$, one needs to estimate constant ($z_1$, $z_0$). constant($z_1$, $z_0$) depends on several factors but it does not depend on the medium, so it could be learned on a training data set (i.e. reference data of step 102') for which $\beta$ is known. This can be achieved with the acquisition of ultrasound data on an attenuation-calibrated phantom (i.e. a reference medium). Let $\delta E_{ref}(z_0, z_1)$ denote the difference of the logarithm of the mean powers measured at depth $z_0$ and $z_1$ on the calibrated phantom, $\beta_{ref}$ its calibrated (known) attenuation, and $\Delta E(z_0, z_1)$ the difference of $\delta E(z_0, z_1)$ and $\delta E_{ref}(z_0, z_1)$. Then, it can be determined $$\Delta E(z_0, z_1) = -4(\beta - \beta_{ref})f_0(z_1 - z_0) + 8(\beta^2 - \beta_{ref}^2)\sigma_f^2(z_1^2 - z_0) \quad (13)$$

Equation (13) may be an example result of the comparison step 104a. Examination of equation (13) (i.e. step 105) reveals that solving $\Delta E(z_0, z_1) = 0$ gives an estimate of $\beta$.

Note that equation (13) could be approximated with:

$$\Delta E(z_0, z_1) = -4 \ast \beta - \beta_{ref} f_0 (z_1 - z_0) \quad (14)$$

This is due to the circumstance that the quadratic term in equation (13) is relatively small and thus neglectable.

It is noted that an important step of this method is to estimate the mean power at depth $z_0$ and $z_1$. The first stage of that estimation process may be to synthetic-beamform in step 103 acquired ultrasound RF data of step 102, the goal being to minimize diffraction impacts. The second stage may consist in estimation the mean power of these beamformed data at a specific depth. However, beamformed data suffer from a well-known problem in ultrasound imaging: they are corrupted by speckle noise. Speckle noise can be smoothed by via spatial averaging, at the expense of spatial resolution. Alternatively, it is possible to use beamforming to obtain beamformed acquisition data. In this case, it becomes possible to use orthogonal apodization on apertures in the synthetic beamforming stage, in order to decrease the variance of the mean power estimate.

The method of the present disclosure, in particular the exemplary method described above, has the following advantages:

- An equation solver can be based both on equation (13) and (14) (e.g. due to the relatively small quadratic term).
- No spectral analysis is performed, hence no need to trade-off time/spatial versus frequency resolution.
- A wideband pulse may be used to minimize diffraction.
- Synthetic beamforming may be performed to ensure both transmit and receive focusing, hence, to decrease diffraction.
- Orthogonal apodizations may be used to smooth speckle to decrease mean power variance estimate, hence, to decrease ultrasound attenuation estimate variance.
- Medium non-dependent parameters such as diffraction or probe sensitivity are learnt on a calibrated phantom.

FIG. 6 shows a diagram of a second exemplary embodiment (local attenuation estimation) of the method according to the present disclosure.

The method of FIG. 6 corresponds to that one of FIG. 4, i.e. in steps 102-104 and 102'-104'. However, (instead of steps 104a and 105 of FIG. 4) in a subsequent step 106 both auto-correlation functions are compared by using a Kalman filter, in order to estimate local attenuation parameter.

The goal of the method of FIG. 6 is to obtain one or several local attenuation parameters, e.g. in the form of a map of local estimation. This means that the basic assumptions are slightly different as compared to that one of the methods of FIG. 4. In particular, it now has to be taken into account that the ultrasound attenuation parameter varies with the spatial location.

Here, it is proposed to estimate the local ultrasound attenuation along axial lines in the depth direction z and to scan along lose lines, i.e. scanning in a similar way as it is usually performed in B-mode imaging.

Hence, the primary goal of this processing is to estimate the ultrasound attenuation parameter on a specific scanning line, i.e. as a function of depth, namely $\beta(z)$. To do so, it is proposed to invert equation (11). Direct inversion of this equation is not straight forward. It is thus proposed to model the logarithm of the mean power as a function of depth by the observation (or measurement) of a noisy state space system.

The logarithm of the mean power as a function of depth may be discretized and may be modelled as the measurement of a discrete-time controlled process that is governed by the following linear stochastic difference equation (15):

$$\begin{cases} x_k = A x_{k-1} + B u_k + w_{k-1} \\ L E_k = H x_k + v_k \end{cases} \quad (15)$$

Where

Xk is the (hidden) state vector
A is the transition matrix
$w_k$ and $v_k$ are the process and measurement noises
H is the measurement matrix
$LE_k$ is the vector containing the difference of the logarithm of the mean powers at index k of the medium under test and the reference medium with known attenuationat depth $k\Delta z$, and the logarithm of the mean power of the reference medium at depth $k\Delta z$
$\Delta_z$ is the depth sampling step
B is the control matrix
$u_k$ is the driving input Let E[k] denote the logarithm of the mean power estimate at depth $k\Delta z$. Taking the Taylor expansion of equation (11) yields:

$$E[k] = E[k-1] + \dot{E}[k-1]\Delta z + \text{constant}(k)$$

$$E[k] = E[k-1] - 4 f_0 \beta[k] \Delta z + \text{constant}(k) \quad (16)$$

Where the approximation may be made:

$$\dot{E}[k] \approx -4 f_0 \beta[k]$$

Let $\Delta E[k]$ denote the difference of the logarithm of the mean powers at index k of the medium under test and reference medium with known attenuation $\beta_{ref}$, a calibrated phantom for example. Then $$\Delta E[k] = \Delta E[k-1] - 4\beta[k-1] f_0 \Delta z + 4\beta_{ref}[k-1] f_0 \Delta z$$

If (constant(k)−constant(k−1)) is included in $v_k$, it is obtained:

$$\Delta E[k] = \Delta E[k-1] - 4\beta[k-1] f_0 \Delta z + 4\beta_{ref}[k-1] f_0 \Delta z + n_1[k]$$

$$\beta[k] = \beta[k-1] + n_2[k]$$

$$E_{ref}[k] = E_{ref}[k-1] - 4\beta_{ref} f_0 \Delta z + n_3[k] \quad (17)$$

Where $E_{ref}$ is the logarithm of the mean power estimated at index k on the reference medium
$n_1[k]$, $n_2[k]$, $n_3[k]$ is the state noise: a zero-mean white Gaussian noise.

Equation (17) can be put in the form of equation (15), if $$x_k = \begin{bmatrix} \Delta E[k] \\ \beta[k] \\ E_{ref}[k] \end{bmatrix} \quad A = \begin{bmatrix} 1 & -4 f_0 \Delta z & 0 \\ 0 & 1 & 0 \\ 0 & 0 & 1 \end{bmatrix}$$

$$H = \begin{bmatrix} 1 & 0 & 1 \\ 0 & 0 & 1 \end{bmatrix} \quad B u_k = 4 f_0 \beta_{ref} \Delta z \begin{bmatrix} 1 \\ 0 \\ -1 \end{bmatrix}$$

It has been found that the Kalman filter provides the optimal estimator of the state vector $x_k$ in equation (15) in the MMSE sense. As a result, it provides the optimal estimator (in the MMSE sense) of $\beta[k]$.

Throughout the description, including the claims, the term "comprising a" should be understood as being synonymous with "comprising at least one" unless otherwise stated. In addition, any range set forth in the description, including the claims should be understood as including its end value(s)

unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

It is intended that the specification and examples be considered as exemplary only, with a true scope of the disclosure being indicated by the following claims.

In summary the method according to the present disclosure as described above allows a more precise attenuation estimation and implies less computational costs what in particular improves a real time computation mode. Further, due to the increased preciseness a decreased variance and thus an increased reproducibility can be achieved.

The invention claimed is:

1. A method for estimating an ultrasonic attenuation parameter of a region in a medium, wherein said method is implemented by a processing unit associated to at least one ultrasound transducer, the method comprising:
   (a) transmitting at least one pulse in the medium by the at least one ultrasound transducer,
   (b) receiving data by the at least one ultrasound transducer in response to the pulse,
   (c) processing the data by the processing unit for providing backscattered acquisition data of the region,
   (d) determining an auto-correlation function of the backscattered acquisition data which is a function of depth in the spatio-temporal domain, the autocorrelation function being determined at a lag of zero, and
   (e) estimating an ultrasonic attenuation parameter based on said auto-correlation function.

2. The method according to claim 1, wherein processing the data comprises performing a beamforming process for providing beamformed acquisition data of the region.

3. The method according to claim 1, wherein estimating the ultrasonic attenuation parameter comprises estimating the ultrasonic attenuation parameter over an interval ($\Delta z$) in the depth direction.

4. The method according to claim 3, wherein estimating the ultrasonic attenuation parameter comprises solving the auto-correlation function for the interval ($\Delta z$).

5. The method according to claim 1, wherein the auto-correlation function of the backscattered acquisition data is a function of depth and of time.

6. The method according to claim 1, wherein determining the autocorrelation function comprises compensating for a residual diffraction pattern in the backscattered acquisition data based on predetermined diffraction reference data.

7. The method according to claim 1, wherein a residual diffraction pattern in the backscattered acquisition data is compensated by applying a method comprising operations (a) to (e) on a reference medium having a predetermined reference ultrasonic attenuation parameter and comparing the auto-correlation functions.

8. The method according to claim 7, wherein comparing the auto-correlation functions comprises calculating a delta function $\Delta E(z_0,z_1)$ between the auto-correlation functions, $z_0$ and $z_1$ being two different depths in the medium and the reference medium, respectively, and solving the delta function $\Delta E(z_0,z_1)=0$ to determine the ultrasonic attenuation parameter of the medium.

9. The method according to claim 6, wherein the predetermined diffraction reference data comprises predetermined parameters for at least two different depths ($z_0,z_1$) in the reference medium.

10. The method according to claim 1, wherein the pulse is a wide band pulse and/or a plurality of pulses.

11. A method for estimating local ultrasonic attenuation parameters of a region in a medium, comprising the method of claim 1, and further comprising for each of a plurality of axial lines in the depth direction (z) within the medium:
   estimating a local ultrasonic attenuation $\beta$ in an equation $F(Ey(z), \beta)=0$, Ey being the auto-correlation function, z the depth, by performing at least one of the following methods:
   modelling the auto-correlation function as a noisy state space model with a driving input,
   regularizing the auto-correlation function by a regularization method comprising: a Tikhonov regularization method, a ridge regression method, and/or Bayesian regression method,
   filtering the auto-correlation function with a Savitzky-Golay filter, a Monte Carlo method, a Singular Spectrum analysis, and
   a compressed sensing and/or sparse sampling method.

12. The method according to claim 11, wherein, in case the auto-correlation function is modelled as a noisy state space model, the driving input comprises the predetermined attenuation parameter of a reference medium.

13. The method according to claim 11, wherein the modelized state space model uses a Kalman filter or a predefined Bayesian method to determine the local ultrasonic attenuation parameter.

14. The method according to claim 11, wherein a reflectivity pattern of the medium is compensated by iterating an EM algorithm on the modelized state space model until a predefined converging threshold is obtained,
   wherein the EM algorithm uses a first Kalman filter which outputs a reflectivity parameter and uses an ultrasound attenuation parameter as a driving input,
   and a second Kalman filter which outputs an ultrasound attenuation parameter and uses a reflectivity parameter as a driving input,
   wherein both filters are connected to respectively use the output of the other one as a driving input.

15. A method for imaging a local ultrasonic attenuation within a region of a medium, comprising the method of claim 11, wherein an attenuation image is built based on the local attenuation parameters.

16. The method for imaging a local ultrasonic attenuation within a region of a medium according to claim 15, further comprising:
   feeding the attenuation image into a machine learning model trained to segment the image into one or several regions of interest which are respectively associated with at least one predefined category.

17. A system for estimating an ultrasonic attenuation parameter of a region in a medium, comprising a processing unit associated to at least one ultrasound transducer, the system being configured to:
   (a) transmit at least one pulse in the medium by the at least one ultrasound transducer,
   (b) acquire data by the at least one ultrasound transducer in response to the pulse,
   (c) process data by the processing unit for providing backscattered acquisition data of the region,
   (d) determine an auto-correlation function of the backscattered acquisition data which is a function of depth in the spatio-temporal domain, the autocorrelation function being determined at a lag of zero, and (e) estimate an ultrasonic attenuation parameter based on said auto-correlation function.

18. The method of claim 1, further comprising building an attenuation map of the region based on the estimated ultrasonic attenuation parameter.

19. The system of claim 17, wherein the system is further configured to build an attenuation map of the region based on the estimated ultrasonic attenuation parameter.

* * * * *

UNITED STATES PATENT AND TRADEMARK OFFICE
CERTIFICATE OF CORRECTION

PATENT NO. : 12,115,026 B2
APPLICATION NO. : 17/371717
DATED : October 15, 2024
INVENTOR(S) : Christophe Fraschini It is certified that error appears in the above-identified patent and that said Letters Patent is hereby corrected as shown below:

In the Specification

Column 9, Line 38, "C:" should read -- c: --.

Column 11, Line 16, "The ACF taken at lag r=0" should read -- The ACF taken at lag $\tau=0$ --.

Column 14, Line 16, "attenuationat" should read -- attenuation at --.

Column 14, Line 18, "$\Delta_z$ is the depth sampling step" should read -- $\Delta z$ is the depth sampling step --.

Signed and Sealed this
Third Day of December, 2024

Katherine Kelly Vidal
*Director of the United States Patent and Trademark Office*